US00PP14519P29

(12) United States Plant Patent
Schräder

(10) Patent No.: US PP14,519 P2
(45) Date of Patent: Feb. 10, 2004

(54) CALIBRACHOA PLANT NAMED 'SUMCALI 01'

(50) Latin Name: *Calibrachoa hybriden*
Varietal Denomination: Sumcali 01

(75) Inventor: Ralf Schräder, Lüdinghausen (DE)

(73) Assignee: Grunewald Veredlings B.V. (NL)

( * ) Notice: Subject to any disclaimer, the term of this patent is extended or adjusted under 35 U.S.C. 154(b) by 50 days.

(21) Appl. No.: 10/341,060

(22) Filed: Jan. 13, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Susan B. McCormick
(74) *Attorney, Agent, or Firm*—Webb Ziesenheim Logsdon Orkin & Hanson, P.C.

(57) ABSTRACT

A new and distinct early flowering Calibrachoa plant with bright violet colored flowers.

2 Drawing Sheets

Botanical classification: *Calibrachoa hybriden.*
Varietal denomination: 'Sumali 01'.

BACKGROUND OF THE INVENTION

The present invention comprises a new and distinct cultivar of Calibrachoa plant known by the varietal name 'Sumcali 01'. The new variety was discovered in June 2000 in a selected breeding program in Lüdinghausen, Germany designed to produce a new variety of Calibrachoa with a trailing character and violet flowers. The new variety was selected from a cross of proprietary unpatented breeding plants 'Celebration Pink' (female parent) and Seedling 05 (male parent). The new variety is a trailing habitus similar to its parents, but differs in flower color from both parents. The new variety was first asexually reproduced in July 2000 by cuttings in Lüdinghausen, Germany. The new variety has been trial and field tested at Lüdinghausen and has been found to retain its distinctive characteristics and remain true to type through successive propagations.

The following trait distinguishes 'Sumcali 01' as a new and distinct cultivar:

1. Flower color.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
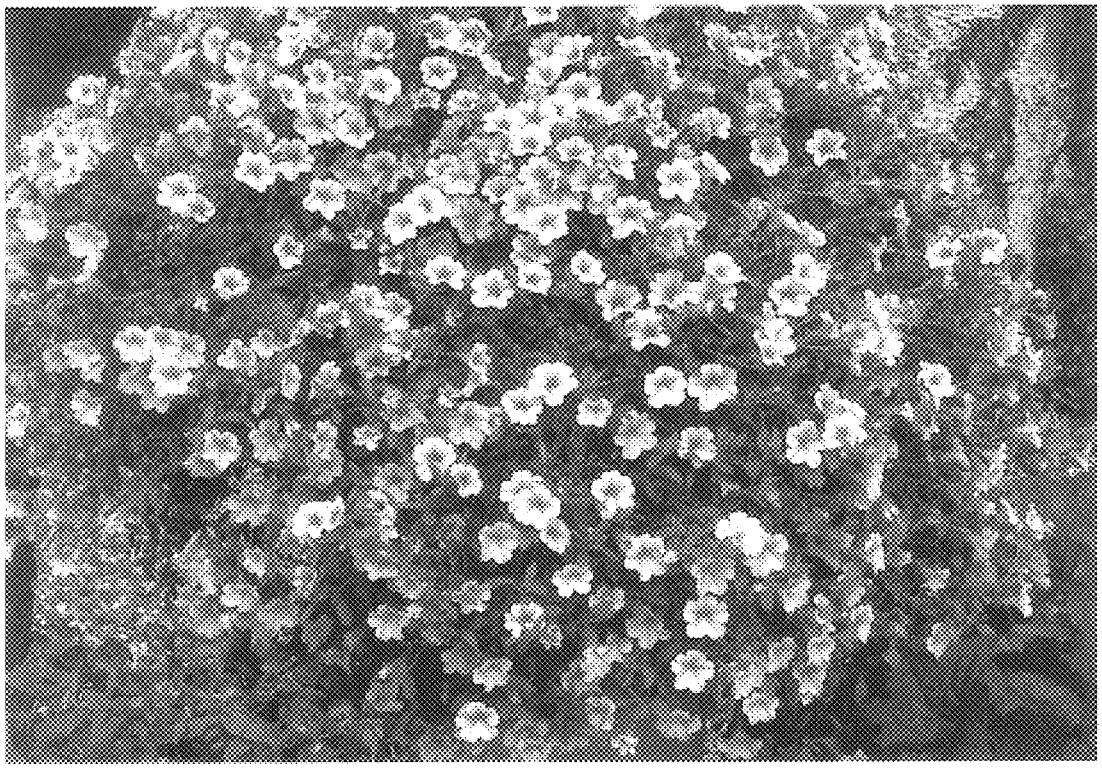
FIG. 1 is a photograph of the plant.
Figure 2:
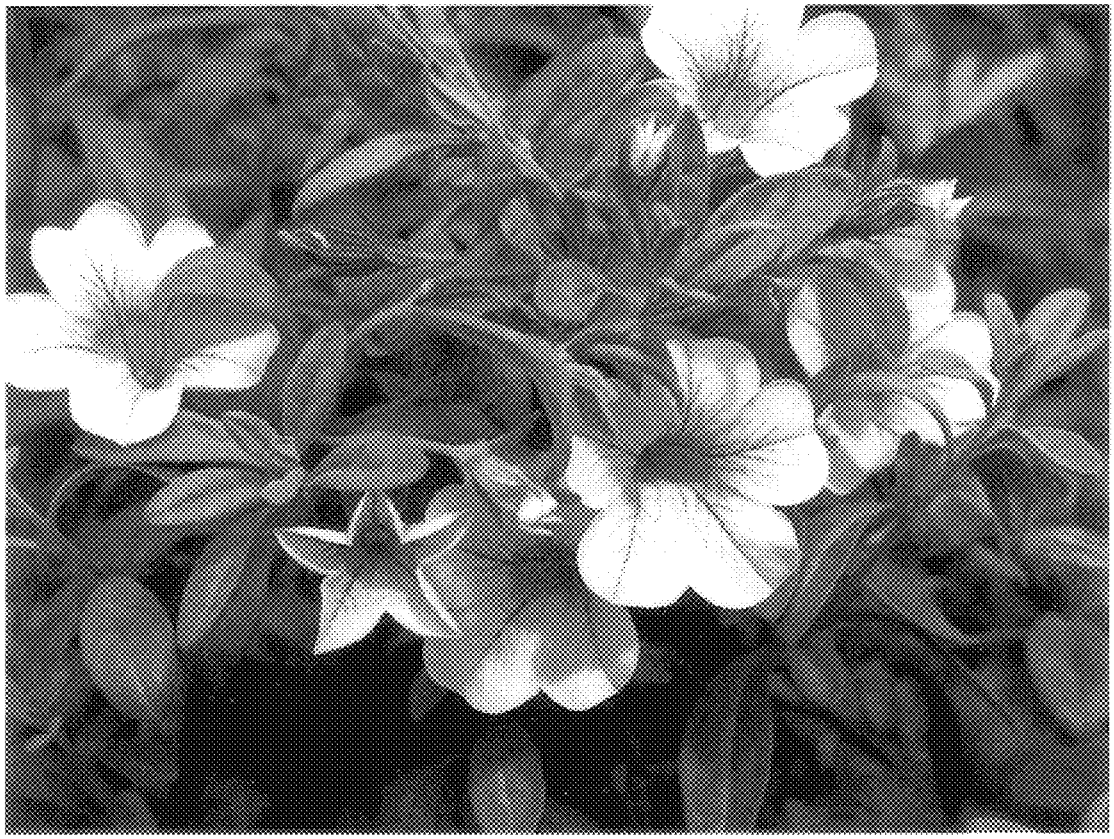
FIG. 2 is a close up view of the blooms of the new plant.

The following detailed description sets forth characteristics of the new cultivar. The data which defines these characteristics were collected by asexual reproductions by cuttings carried out in Lüdinghausen, Germany. Plants for the description were 10 weeks old, grown in a greenhouse in 11 cm containers at 16° C. temperature. The color readings were taken in a greenhouse under natural light. Color references are primarily to The 2001 R.H.S. Colour Chart of The Royal Horticultural Society of London.

PLANT

Form: Spreading.
Height (from soil to top of flowers): 10 cm.
Diameter: 40–50 cm.
Vigor: Middle.
Roots:
- *Habit.*—Mounded.
- *Time to initiate roots.*—10 days at 18° C.
- *Time to develop roots.*—15 days at 18° C.

Branching habit: Hanging.
Lateral branches:
- *Form.*—Hanging.
- *Color.*—141D.
- *Texture.*—Smooth.
- *Diameter.*—1.5 mm.
- *Internode length.*—3 mm.
- *Quantity.*—Good.

Foliage:
- *Arrangement.*—Alternate.
- *Number of leaves per branch.*—20–25.
- *Size of leaf.*—Length: 18 mm. Width: 9 mm.
- *Shape of leaf.*—Lanceolate.
- *Shape of apex.*—Obtuse.
- *Shape of base.*—Obtuse.
- *Texture.*—Smooth.
- *Aspect.*—Lanceolate.
- *Margin.*—Entire.
- *Color.*—Young leaves: Upper surface: 138A. Lower surface: 138A. Mature leaves: Upper surface: N138C. Lower surface: N138B.
- *Petiole.*—Length: 2 mm. Diameter: 1 mm. Color: 144B.
- *Veins.*—Color: Upper surface: 143C. Lower surface: 143C.

FLOWER

Natural flowering season: Spring to autumn.
Flower type and habit: Normal.
Number of flowers per plant: 60–70.
Corolla:
- *Diameter.*—3.4 mm.
- *Flower tube length.*—15 mm.
- *Flower tube diameter at distal end.*—8 mm.
- *Flower tube diameter at proximal end.*—3 mm.

*Petal length from throat.*—8 mm.
*Petal width.*—12 mm.
*Petal quantity.*—5 parts fused at base.
*Petal apex shape.*—Oval.
*Texture.*—Smooth.
*Color.*—When opening: Upper surface: 84D with veins of 83A. Lower surface: 84C with veins of 83A. Fully opened: Upper surface: 84D with veins of 83A. Lower surface: 84D with veins of 83A.
*Flower throat* (*inside*).—6C.
*Flower throat, vein.*—200B.
*Flower tube* (*outside*).—149D.
*Flower tube, vein.*—200D.
*Petal color, fading to.*—N88C.

Peduncle:
*Length.*—14 mm.
*Diameter.*—1 mm.
*Color.*—144A.
*Orientation.*—Angled.
*Strength.*—Middle.

Bud:
*Shape.*—Lanceolate.
*Length.*—11 mm.
*Diameter.*—4 mm.
*Color.*—146A.

Calyx:
*Shape.*—5 parted; lanceolate.
*Length.*—13 mm.
*Diameter.*—8–10 mm.
*Sepal shape.*—Lanceolate; acuminate.
*Sepal margin.*—Entire.
*Sepal texture.*—Smooth.
*Sepal color.*—Upper surface: 144A. Lower surface: 144A.

Disease resistance: No resistance to diseases noted to date.
Fragrance: None.
Weather tolerance: Middle to strong.
Lasting quality: Continuously good.
Seed production: Seldom.

REPRODUCTIVE ORGANS

Stamens:
*Number.*—5.
*Filament length.*—2–3 mm.
*Anthers.*—Shape: Round. Length: 0.5 mm. Color: 10B.
*Pollen.*—Color: 10D. Amount: Minimal.

Pistil:
*Length.*—2–3 mm.
*Style.*—Length: 0.2 mm. Color: 146B.
*Stigma.*—Shape: Oval. Color: 146B. Ovary color: N92C.

I claim:

1. A new and distinct variety of Calibrachoa plant substantially as shown and described.

* * * * *